United States Patent
Houde et al.

(10) Patent No.: US 8,884,181 B2
(45) Date of Patent: Nov. 11, 2014

(54) METHOD OF GENERATING LOW-ENERGY SECONDARY ELECTRONS FOR APPLICATIONS IN BIOLOGICAL SCIENCES, RADIOCHEMISTRY, AND CHEMISTRY OF POLYMERS AND PHYSICS OF RADIOTHERAPY

(71) Applicant: Société de Commercialisation des Produits de la Recherche Appliquée—SOCPRA SC, Sherbrooke (CA)

(72) Inventors: Daniel Houde, Sherbrooke (CA); Ridthee Meesat, Bangkok (TH); Jean-François Allard, Princeville (CA); Tiberius Brastaviceanu, Montreal (CA)

(73) Assignee: SOCPRA-Sciences Sante et Humaines S.E.C., Sherbrooke (CA)

( * ) Notice: Subject to any disclaimer, the term of this patent is extended or adjusted under 35 U.S.C. 154(b) by 0 days.

(21) Appl. No.: 13/786,050

(22) Filed: Mar. 5, 2013

(65) Prior Publication Data
US 2013/0181142 A1    Jul. 18, 2013

Related U.S. Application Data

(63) Continuation of application No. 13/580,038, filed as application No. PCT/CA2011/000273 on Mar. 11, 2011, now abandoned.

(60) Provisional application No. 61/313,553, filed on Mar. 12, 2010.

(51) Int. Cl.
| | |
|---|---|
| *H01J 37/00* | (2006.01) |
| *G01N 21/39* | (2006.01) |
| *G21K 5/08* | (2006.01) |
| *B23K 26/02* | (2014.01) |
| *A61N 5/10* | (2006.01) |
| *A61L 2/08* | (2006.01) |
| *A61B 18/20* | (2006.01) |
| *A61N 5/06* | (2006.01) |
| *G21K 5/00* | (2006.01) |

(52) U.S. Cl.
CPC .. *G21K 5/00* (2013.01); *A61N 5/10* (2013.01); *A61L 2/087* (2013.01); *A61B 18/20* (2013.01); *A61N 5/0624* (2013.01); *A61N 2005/1088* (2013.01); *A61N 2005/1089* (2013.01)
USPC .............. 219/121.6; 219/121.83; 250/453.11; 250/307; 250/310; 250/336.1

(58) Field of Classification Search
CPC ........... H01J 37/00; G01N 21/39; G21K 5/08; B23K 26/02
USPC ......................... 250/453.11, 307, 310, 336.1; 219/121.6, 121.83
See application file for complete search history.

(56) References Cited

U.S. PATENT DOCUMENTS

| | | | |
|---|---|---|---|
| 7,728,295 B2 * | 6/2010 | Miles et al. ................ | 250/336.1 |
| 2008/0245964 A1 | 10/2008 | Miles et al. | |

(Continued)

FOREIGN PATENT DOCUMENTS

WO        03/021212        3/2003

OTHER PUBLICATIONS

Bothe et al., "Single-and Double-Strand Break Formation in Double-Stranded DNA Upon Nanosecond Laser-Induced Photoionization", Photochemistry and Photobiology, vol. 52, No. 5, Feb. 1, 1990, pp. 949-959.

(Continued)

*Primary Examiner* — Nikita Wells
(74) *Attorney, Agent, or Firm* — Fay Kaplun & Marcin, LLP

(57) ABSTRACT

The present disclosure relates to a method and a system for generating low-energy electrons in a biological material. The biological material is held in position by a support. Laser beam pulses are directed by a focusing mechanism toward a region of interest within the biological material. This generates filaments of low-energy electrons within the region of interest. The method and system may be used for radiotherapy, radiochemistry, sterilization, nanoparticle coating, nanoparticle generation, and like uses.

27 Claims, 5 Drawing Sheets

(56) References Cited

U.S. PATENT DOCUMENTS

2011/0284744 A1* 11/2011 Zewail et al. ............... 250/307
2012/0120226 A1* 5/2012 de Jonge ..................... 348/80

OTHER PUBLICATIONS

Pimblott et al., "Production of low-energy electrons by ionizing radiation," Rad. Phys. and Chemistry, vol. 76, 2007, pp. 1244-1247.
Meesungnoen et al., "Low-energy electron penetration range in liquid Water," Rad. Res, vol. 158, 2002, pp. 657-660.
Chin et al.,"Generation of H2, O2 and H2O2 from water by the use of femtosecond laser pulses and the possibility of laser sterilization,"Appl. Opt., vol. 35, No. 6, 1996, pp. 907-911.
Meesat et al., *"Fricke and polymer gel dosimetry of femtosecond laser pulse filamentation and radiation chemical effects of laser on thymidine solutions. Comparaison with $^{60}$Co irradiation,"* Research Annual Meeting, Savannah, GA, Oct. 2009, 6 sheets.
Pépin et al., "Evidence for resonance-enhanced multiphoton ionization of liquid water using 2 eV laser light: variation of hydrated electron absorbance with femtosecond pulse intensity", Phys. Rev. Lett., vol. 69, No. 23, 1992, pp. 3389-3392.
Pépin et al., "Femtosecond kinetics measurements of excess electrons in methanol: substantiation for a hybrid salvation mechanism". J. Phys. Chem., vol. 98, 1994, pp. 7009-7013.
Zheng et al., "Glycosidic Bond Cliveage of Thymidine by Low-Energy Electrons," J.A.C.S., vol. 126, 2004, pp. 1002-1003.
Lepage, et al.,"The relationship between radiation-induced chemical processes and transverse relaxation times in polymer gel dosimeters," Phys. Med. Biol, vol. 46, 2001, pp. 1061-1074.
Olszanski et al., "The IRS Fricke Dosimetry System", Ionizing Radiation Standards, Institute for National Measurement Standards, National Research Council, Aug. 2002, 70 sheets.
Autsavapromporn et al., "Monte Carlo simulation study of the effects of acidity and LET on the primary free-radical and molecular yields of water radiolysis—Application to the Fricke dosimeter", Can. J. Chem, vol. 85, 2007, pp. 214-229.
Meesat et al., "Femtosecond laser pulse filamentation characterized by polymer gel dosimetry and Fricke dosimetry", IC3DDose: The 6th International Conference of 3D Radiation Dosimetry, Journal of Physics: Conference Series, vol. 250, 2010, 012077, 6 sheets.
Boudaïffa et al., "Resonant Formation of DNA Strands Breaks by Low-Energy (3 to 20 eV) Electrons", Science, vol. 287, Mar. 3, 2000, pp. 1658-1660.
Chin et al., "The propagation of powerful femtosecond laser pulses in optical media: physics, applications, and new challenges", Can. J. Phys, vol. 83, 2005, pp. 863-905.
Couairon et al., "Femtosecond filamentation in transparent media", Physics Reports, vol. 441, 2007, pp. 47-189.
Messat et al., " Cancer Radiotherapy based on femtosecond IR laser-beam filamentation yielding ultra-high dose rates and zero entrance dose," PNAS, Jul. 27, 2012, 9 sheets.
Zhu et al., "Phenomenon and Research Progress of fs Laser Pulse and Its Interaction with water," Laser & Optoelectronics Progress, vol. 40, No. 11, Nov. 2003, 2 sheets.
Di et al., "Principles and Applications of the Femtosecond Laser in the Cell Nanosurgery," ACTA Laser Biology Sinica, Vo. 17, No. 2, Apr. 2008, pp. 1-13.

\* cited by examiner

METHOD OF GENERATING LOW-ENERGY SECONDARY ELECTRONS FOR APPLICATIONS IN BIOLOGICAL SCIENCES, RADIOCHEMISTRY, AND CHEMISTRY OF POLYMERS AND PHYSICS OF RADIOTHERAPY

TECHNICAL FIELD

The present disclosure relates to generation of low-energy secondary electrons. More specifically, the present disclosure relates to a method and a system for generating low-energy electrons in a biological material.

BACKGROUND

Secondary electrons are electrons generated as ionization products. They are called "secondary" because they are generated by other radiation, called primary radiation. This primary radiation may be in the form of ions, electrons, or photons with sufficiently high energy to exceed an ionization potential. Photoelectrons are an example of secondary electrons where the primary radiation consists of photons. Low-energy secondary electrons play a crucial role in the degradation of high-energy ionizing radiation such as X-rays, γ-photons or charged particles. Low-energy secondary electrons are a means to define the geometry of the radiation track.

SUMMARY

The present disclosure broadly relates to generation and applications of low-energy secondary electrons.

Therefore, according to the present disclosure, there is provided a method for generating low-energy electrons in a biological material. The method comprises a step of supporting the biological material. Laser beam pulses are generated. The laser beam pulses are focused pulses toward a region of interest within the biological material to generate filaments of low-energy electrons.

According to the present disclosure, there is also provided a system for generating low-energy electrons in a biological material. The system comprises a support for the biological material, a pulsed laser and a focusing mechanism. The focusing mechanism directs laser beam pulses toward a region of interest within the biological material to generate filaments of low-energy electrons.

The foregoing and other features will become more apparent upon reading of the following non-restrictive description of illustrative embodiments thereof, given by way of example only with reference to the accompanying drawings.

BRIEF DESCRIPTION OF THE DRAWINGS

Embodiments of the disclosure will be described by way of example only with reference to the accompanying drawings, in which.

DETAILED DESCRIPTION

Figure 1:
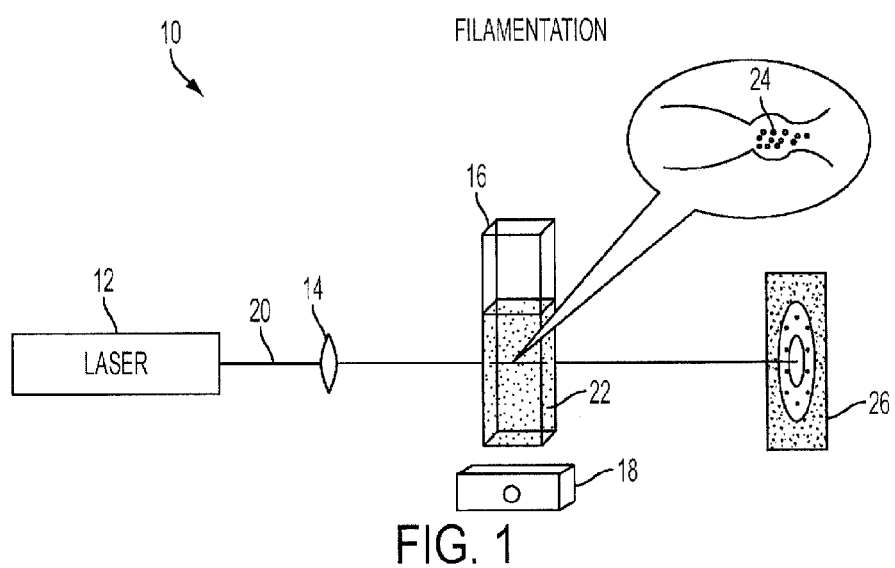
FIG. 1 is schematic view of a laboratory system for generating femtosecond laser filamentation in accordance with an illustrative embodiment.

Generally stated, the non-limitative illustrative embodiment of the present disclosure provides a method and a system for generating low-energy secondary electrons for applications in biological sciences, medical applications, radiochemistry, and chemistry of polymers and physics of radiotherapy. More specifically, the low-energy secondary electrons are produced using femtosecond (fs) laser filamentation.

Although femtosecond laser filamentation (FLF) is a well-known process, it has seldom been used for radiolysis of water [7]. It has been discovered that low-energy electrons (LEE) in FLF and ionization radiation are radiochemically equivalent for applications in biological sciences, radiochemistry, and chemistry of polymers and physics of radiotherapy. The LEE are generated by laser pulses and are then directly recombined or solvated in liquid, in about 300 to 500 fs in water.

In the degradation of high-energy ionizing radiation like X-rays, γ photons or charged particles such as, for example, accelerated electrons or heavier charged particles, low-energy secondary electrons serve to define a geometry of a radiation track. They consist of highly anisotropic ionization energy deposition of secondary electrons with energy between about 1 and 20 eV, for example about $5 \times 10^4$ electrons/MeV [1]. In this energy range, an electron penetration range in water is in the order of 10 nanometers (nm) [2].

Demonstration of genotoxic action of low-energy electrons on fundamental biological molecules, such as for example deoxyribonucleic acid (DNA), film of biological molecules, and similar compounds, may be achieved in ultra-high vacuum conditions [5]. To extend this demonstration, an anisotropic concentration of low-energy electrons in a macroscopic volume of water, in the order of a cubic centimeter ($cm^3$) of water, is generated using intense, ultra-short laser pulses, which lead to self-focusing and filamentation. The physical origin of the formation of filaments is well understood. Briefly, self-focusing is an induced lens effect, resulting from wavefront distortion self-inflicted on a beam while traversing a nonlinear medium. Consequently, as the beam travels in the nonlinear medium, an original plane wavefront of the beam gets progressively more distorted. The distortion is similar to that imposed on the beam by a positive lens. Since the optical ray propagation is in the direction perpendicular to the wavefront, the beam appears to focus by itself. This degenerative process, in which the positive lens effect increases with intensity, is stabilized in the femtosecond regime by the generation of electrons forming a filament. Electrons are produced by multiphoton or tunnel ionization and are further accelerated by an electric field of the pulse in an inverse Bremstrahlung effect. When they acquire enough kinetic energy, for example 6.5 eV in the case of water, the electrons give rise to a second generation of electrons by impact ionization of other molecules in an avalanche-like process. This linear distribution of electrons formed in the filament, in the range of $10^{16}$-$10^{18}$ electrons per $cm^3$, transfers their excess energy to surrounding water molecules, which leads to the generation in a self-focusing region of chemically reactive species such as $e_{aq}$, $H^*$, $O^*$, and $^*OH$, and recombination products $H_2$, $O_2$, $H_2O$, and $O_2^*$— (or $HO_2^*$, $pK_a$=4.8).

There does not exist in the literature any mention of real time measurements of the presence of LEE in a filament. However, as LEE are generated in filamentation, solvated electrons become measureable along the filament. Pump-probe measurements may be used for this purpose. Solvated electrons have an optical spectrum measurable by a femtosecond pump-probe technique. The presence of solvated electrons along the filament may be measured using a delay of 50 picoseconds (ps) between an 800 nm pump pulse having a 100 fs pulse duration, which generates the filament, and an optical probe of a 125 fs pulse duration at 720 nm from an optical parametric amplifier (OPA). Scanning a position of a pump lens changes the position of the filament in a linear direction. A characteristic intensity evolution of the length of the filament in FLF has been observed from the pump-probe scan measurement in function of the pump pulse intensity [6].

Figure 6:
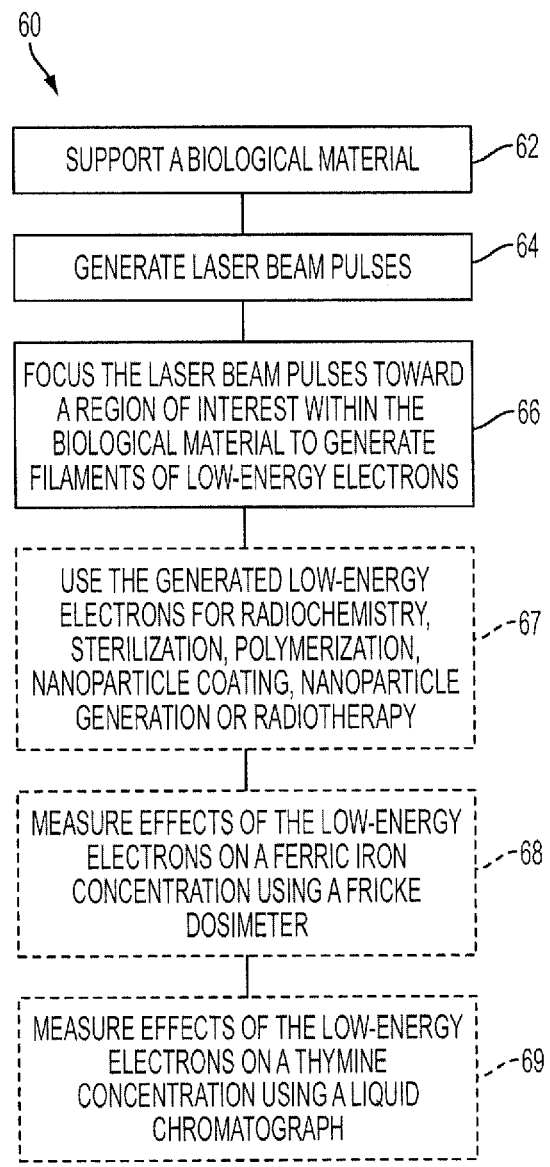
FIG. 6 shows steps of an exemplary method for generating low-energy electrons in a biological material.

Referring to FIG. 1, which is schematic view of a laboratory system for generating femtosecond laser filamentation in accordance with an illustrative embodiment, a system 10 comprises a laser 12 producing a beam 20 aimed at a region of interest (ROI) in an optical path cuvette 16 through a focusing mechanism 14. Concurrently, FIG. 6 shows steps of an exemplary method for generating low-energy electrons in a biological material. A sequence 60 of steps, as shown on FIG. 6, will be described concurrently with details of FIG. 1 and with details of the following Figures. Some of the steps of sequence 60 may be present in some embodiments and not in other embodiments. Some of the steps may be executed in a different order compared to that shown on FIG. 6.

The optical path cuvette 16 supports a biological material (step 62), used as a laboratory sample, contained in an aqueous solution 22. The cuvette 16 is positioned on a magnetic steering device 18 in order to homogenize the solution 22 between pulses. The laser generates laser beam pulses (step 64), which are focused by the focusing mechanism 14 towards the ROI to generate filaments of low-energy electrons (not shown) within the ROI (step 66). The filaments have a length of about one (1) cm, producing low-energy electrons 24 in the solution 22. A detector 26, for example a streak camera, detects an image of the beam 20 diffracted within the solution 22. A resulting image may be used for time-resolved spectroscopy or for resonance imaging (MRI) analysis.

The laser 12 may be, for example, a Spectra-Physics® 300-750 mW femtosecond Regenerative Ti-Sapphire laser having an optical parametric amplifier (OPA) and harmonic generator (HG), used at 300 μJ/pulse, 100 fs pulses at 800 nm and at 1 kHz repetition rate. The focusing mechanism 14 may have a focal lens of f=30 cm. This setup results in the production of filaments of about one (1) cm in a one (1) cm optical path cuvette 16. In another embodiment, a High Power Spitfire PRO__35F-1KXP, 35 fs Ti:Sapphire regenerative laser, 4 watts at 1 kHz and at 800 nm, may be used, along with a AXIS-PV Streak Camera from Axis Photonique Inc. Details of a laser source used in the context of the present disclosure may vary; characteristics of the laser 12 as presented hereinabove are exemplary and not intended to limit the scope of the present disclosure.

Examples of applications of LEE in FLF include the following applications. These applications are generally illustrated on FIG. 6, step 67.

Radiotherapy

Figure 2:
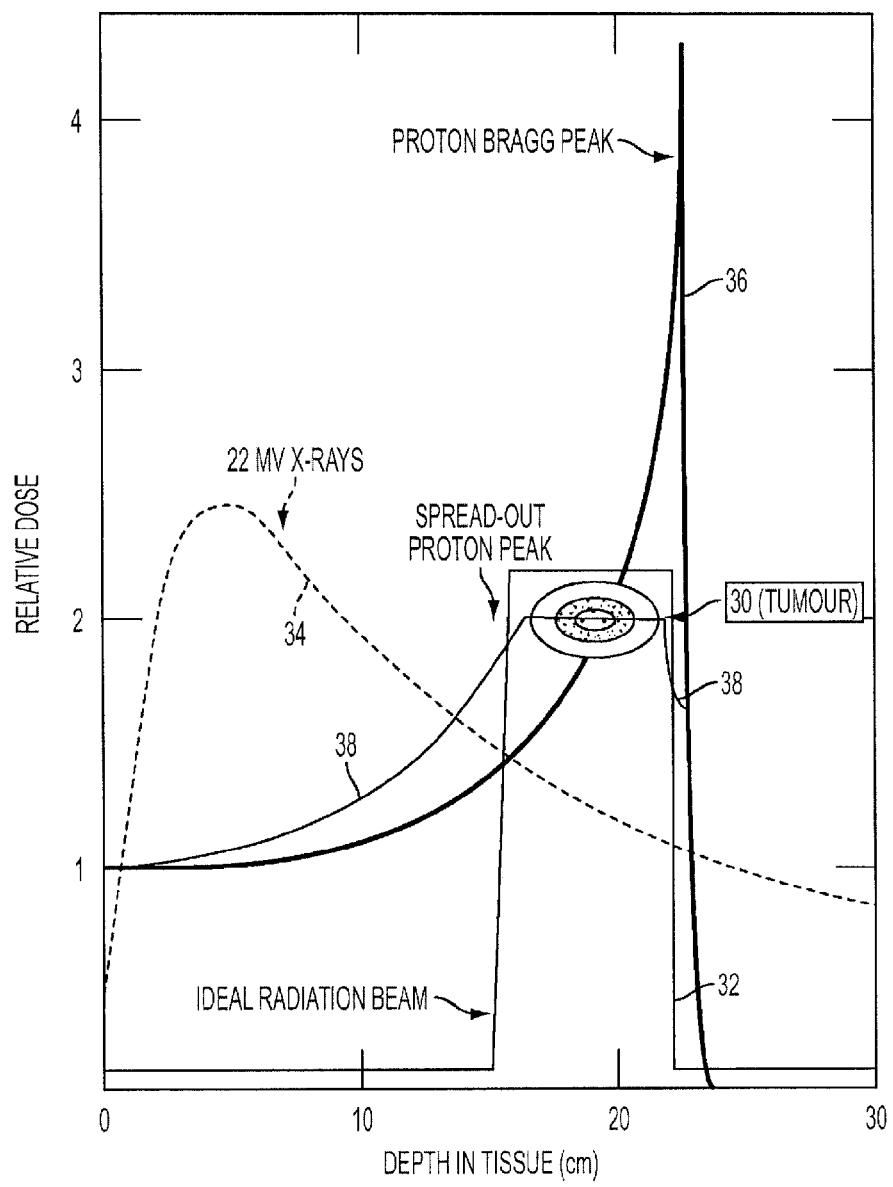
FIG. 2 is a graph of a relative dose distribution using X-rays, proton Bragg peak and an effective spread-out proton peak for radiotherapy treatment.

One of the applications of the control of the distribution of the LEE is a better dose distribution of radiation interaction in radiotherapy. FIG. 2 is a graph of a relative dose distribution using X-rays, proton Bragg peak and an effective spread-out proton peak for radiotherapy treatment. The present disclosure proposes to replace the use of X-ray therapy or proton therapy with an LEE-based approach. On FIG. 2, a tumor 30 may be treated using X-rays having a distribution curve 34, or using protons having a Bragg peak 36 and being further spread along curve 38. Using instead the LEE-based approach allows to obtain a near ideal dose distribution 32 around the tumor 30. For this purpose, a local distribution of LEE in a macroscopic volume ($\sim cm^3$) of water needs to be controlled. LEE cannot be injected deeply in a large volume of water. Anisotropic LEE is therefore locally generated with a control of the energy of these LEE and of the geometry of the distribution. The laser 12 producing the beam 20 and the focusing mechanism 14—or an equivalent focusing mechanism—from FIG. 1 are used to direct laser pulses toward a properly supported and immobilized region of interest (ROI), which replaces the laboratory sample of FIG. 1. This modified system is thus a radiation dose delivery system. The ROI, for example bodily tissues or other biological material, comprises aqueous components and may further comprise a tumor or like aspect that requires treatment. It is through parameter adjustment of the laser 12 and/or of the focusing mechanism 14 that the filaments of anisotropic LEE are generated in proper location, with desired energy and distribution geometry.

Filaments are analogue of tracks with an important difference. Diameters of filaments in condensed matter are around 10 to 100 μm. Demonstration of the presence of $H_2$ and $H_2O_2$ is well-known. Although stabilization of the filament is due to the presence of electrons, no time-resolved measurement of this presence has earlier been publicly made. The present disclosure therefore suggests to measure femtosecond time-resolved presence of the $e_{aq}$ along the filament. A Fricke dosimeter (not shown), also called a ferrous sulphate dosimeter, measures oxidation conversion of ferrous ions ($Fe^{2+}$) to ferric ions ($Fe^{3+}$) by ionizing radiation having produced $e_{aq}$, *OH, $HO_2$*, $H_2O_2$, and the like, in water. Increase of ferric ions concentration in filaments may be measured spectrophotometrically (FIG. 6, step 68) at an optical absorption maximum at 303 nm. 6.5 eV electrons, which correspond to a maximum energy of the LEE in water, have linear energy transfer (LET) of 1 keV/μm [2] and $G(Fe^{3+})$ of 15.3 molecules/100 eV ($G(Fe^{3+})$) for 1 keV/μm radiation [3]. Those values correspond to radiation from a Cesium 137 ($^{137}Cs$) Gammacell® Elan 3000 irradiator from Best Theratronics Ltd. In view of those characteristics, the Fricke dosimeter is an appropriate tool to compare radiation equivalent of FLF and Gamma irradiation, also called "Gammaknife".

Figure 3:
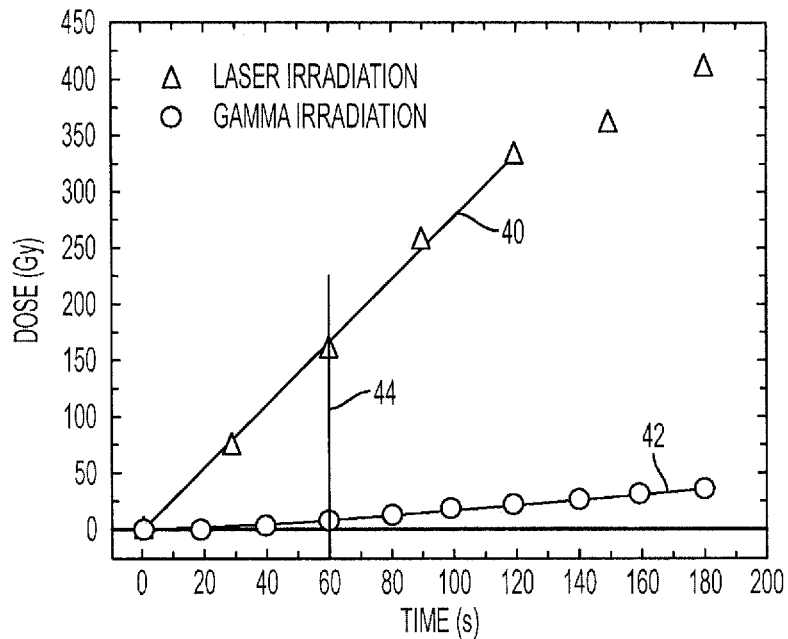
FIG. 3 is a graph of an irradiation dose deposition equivalent of femtosecond laser filamentation and Gamma irradiation as a function of time.

Referring now to FIG. 3, there is shown a graph of an irradiation dose deposition equivalent of intense femtosecond laser filamentation and Gamma irradiation as a function of time. A 1 kHz repetition rate is used for the laser 12 of FIG. 1. FIG. 3 shows a curve 40 for the laser irradiation and a curve 32 for the Gamma irradiation. At a 60-second time point 44, a dose rate of 168 Gy/min is obtained using FLF, compared to 12 Gy/min using the $^{137}Cs$ irradiator. Comparison of measurements obtained with the Fricke dosimeter with those obtained from Gamma irradiation thus provides a dose rate for the filaments. It may be observed that the irradiation dose deposition equivalent of intense femtosecond laser filamentation could also be compared with results obtained from Cobalt 60 ($^{60}Co$) irradiation.

Polyacrylamine gel (PAG) dosimetry is used in three-dimensional (3D) magnetic MRI of radiation. PAG is composed of 2 monomers (3% of acrylamide, 3% of bisacrylamine) in 5% gelatin and 89% of water. LEE may also be generated in PAG and in like polymers. Because radiologic properties of gel dosimeter are equivalent to properties of tissues, radiation-induced polymerization of the comonomers generates a fast-relaxing insoluble polymer. Filament diameters may be estimated in PAG imaged by MRI, whereby PAG effectively becomes a 3D dosimeter. In laboratory tests, optical and MRI imaging of energy deposition in the PAG is obtainable and an image of the LEE filamentation in a polymer volume has been observed. Production, analysis and control of a dose deposition of LEE in FLF in PAG media, in function of optical irradiation conditions involving control of optical parameters and pulse duration, allow analysis of related fundamental physical and chemical processes and a determination of an ideal dose deposition for radiotherapy treatment.

The use of PAG dosimeter is useful in obtaining 3D imaging of energy deposition, for MRI imaging and for optical imaging. PAG material is a radiological equivalent of tissues, especially for MRI imaging. PAG is a good prototype material to test the physics of radiotherapy without using actual tissues and may be put to use for demonstrating the capability of FLF to produce an ideal radiation beam for dose deposition in radiotherapy treatment. For a specific optical setting, using a fixed focal lens, the length of a produced filament depends of the instantaneous laser intensity. The local intensity dependence may be controlled by pulse duration. Adjusting the pulse duration so that an image does not start in the front of a cuvette containing the PAG allows adjusting the beginning of the filamentation and thus the dose deposition. Modifying the optical setting allows changing the end of the filamentation. In an approximation, it is estimated that a multifilament diameter in PAG material is at a maximum of 625 µm diameter, an accuracy of this measure being limited by imaging resolution of MRI techniques, which in turn are controlled by a magnetic field of seven (7) tesla and by the size of the cuvette. In gas phase, the diameter of a monofilament is evaluated at 10 µm [6]. The diameter of a monofilament may also be limited by the chemistry of polymerization and by set-up of the optical system, including parameterization of filtering and of pulse duration. This polymerization is controlled by a chain reaction and by a distribution of a radical produced by ionization.

In an embodiment, MRI analysis of energy deposition using monofilament and deposition of energy using Gammaknife in PAG may be compared. In another embodiment, time-resolved spectroscopy and optical imaging, for example using a streak camera, may be used to measure a time-resolved fluorescence spectroscopy during monofilament formation. Analysis may be made in function of oxygen concentration and in function of laser pulse duration, whereby conditions for controlling energy deposition in PAG may be optimized. In yet another embodiment, simultaneous control of pulse duration and focalization, for example using a deformable mirror, in monofilament and multifilament conditions, while using a Gammaknife reference, allows optimal calibration of a dose deposition using MRI.

Radiochemistry

Figure 4:
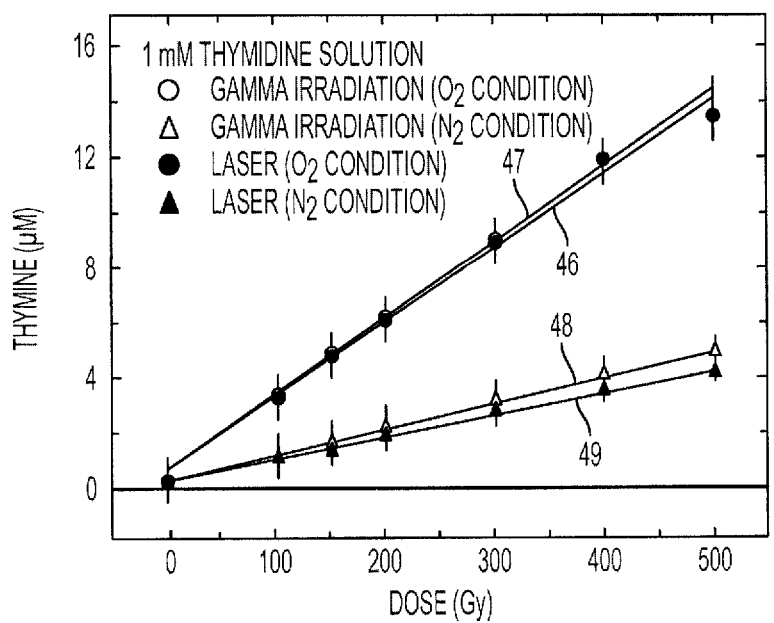
FIG. 4 is a graph of a comparative concentration of thymine production as a function of an irradiation dose.

Another application of the control of the distribution of the LEE is radiochemistry. This is illustrated using a thymidine solution [4]. It is well established that LEE, in a range of 3-100 eV, cleave thymidine in a molecule of thymine and a 2-deoxy-D-ribose. Referring to FIG. 4, which is a graph of a comparative concentration of thymine production as a function of an irradiation dose, the concentration of thymine may be obtained using a chromatograph (not shown) by measuring (FIG. 6, step 69) the thymine concentration production using high performance liquid chromatography (HPLC) in the ultraviolet range [4]. A chemical equivalence action of LEE in FLF and Gamma irradiation is thus obtained. Curves on FIG. 4 show very similar results obtained in the presence of oxygen ($O_2$ condition) with Gamma irradiation (curve 46) and with FLF (curve 47). Likewise, FIG. 4 shows very similar results obtained in the absence of oxygen ($N_2$ condition) with Gamma irradiation (curve 48) and with FLF (curve 49).

Sterilization

Figure 5A:
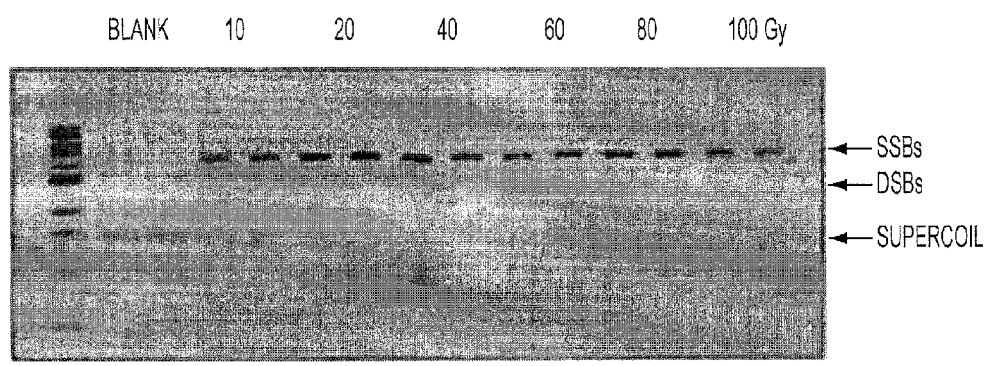
FIG. 5 is a graph of agarose gel electrophoresis, using (a) Gamma irradiation and (b) femtosecond laser filamentation irradiation, of plasmid DNA.
Figure 5B:
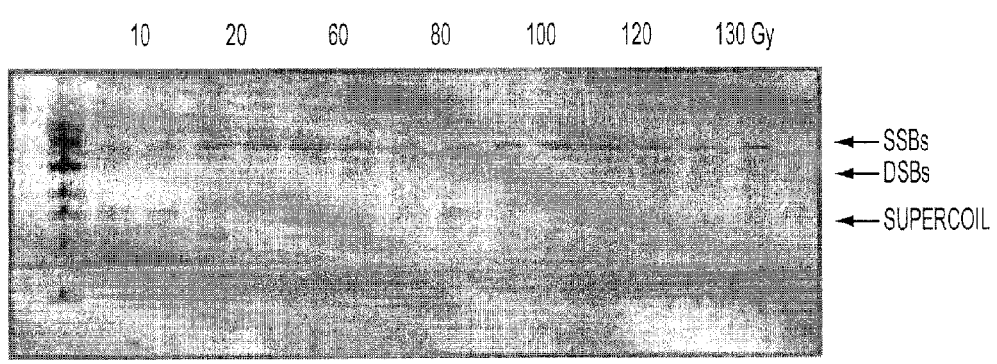

Yet another application of the control of the distribution of the LEE is radiation-induced damage in tissue for sterilization purposes. This is illustrated using *E. Coli* cells in water. FIG. 5 is a graph of agarose gel electrophoresis, using (a) Gamma irradiation and (b) femtosecond laser filamentation irradiation, of pGEM-3Zf(−) plasmid DNA. The plasmid DNA (3197 bp, Promega) was extracted form *E. coli* DH5α and purified with the QIAfilter Plasmid Giga Kit (Qiagen). Agarose gel electropholysis was used to show that 95% of DNA was initially in the supercoil form, 4% was in the concatemeric form and 1% was in the circular form. The DNA was dissolved in de-ionized water. The concentration of DNA was measured by its UV absorption at 260 nm, assuming a molar extinction of 7120 $mol^{-1}/cm^{-1}$ at pH7.0. The amount of DNA in each sample that was used for irradiations was 200 ng/ml. After Gamma irradiation (12 Gy/min) and filamentary laser irradiation (168 Gy/min), plasmid DNA was extracted [5] and analyzed by agarose gel electrophoresis and quantified as supercoil (undamaged) DNA, single strand break (SSB) and double strand break (DSB), which results are shown in FIG. 5 (*a*). FIG. 5 (*b*) shows the results obtained by LEE in FLF (462 Gy/min), using a Ce dosimeter adapted for high dose irradiation. Comparing results obtained in FIG. 5 for Gamma irradiation (a) and for LEE in FLF (b) demonstrates that LEE in FLF produces a radiochemical equivalent action to that obtained using ionization radiation in certain type of living cells. This confirms that LEE in FLF and ionization radiation are radiochemically equivalent for application in biological sciences, radiochemistry, and chemistry of polymers and physics or radiotherapy.

LEE in FLF may be used, for example, for the sterilization of injectable drugs and the decontamination of hospital waste water.

Polymerization

A further application of the control of the distribution of the LEE is radiation-induced polymerization of the co-monomers generates a fast-relaxing insoluble polymer.

Nanoparticle Coating

The polymerization may be used for coating nanoparticles in solution.

Nanoparticle Generation

FLF may be used to generate gold nanoparticles in solution.

Those of ordinary skill in the art will readily appreciate that the above mentioned fields of application of LEE in FLF are exemplary and are not intended to limit the scope of the present disclosure. Generating low-energy secondary electrons as taught herein may be advantageously applied in other fields of endeavor.

Although the present disclosure has been described hereinabove by way of non-restrictive, illustrative embodiments thereof, these embodiments may be modified at will within the scope of the appended claims without departing from the spirit and nature of the present disclosure.

REFERENCES

[1] Simon M. Pimblott, Jay A. LaVerne, *Production of low-energy electrons by ionizing radiation*, Rad. Phys. and Chemistry, 76, 1244-1247 (2007).

[2] J. Meesungnoen, J.-P. Jay-Gerin, A. Filali-Mouhim, S. Mankhetkom, *Low-energy penetration range in liquid Water*, Rad. Res 158, 657-660 (2002).

[3] N. Austsavapromprom, J. Meesungnoen, 1. Plante, J.-P. Jay-Gerin, *Monte-Carlo study of the effects of acidity and LET on primary free-radical and molecular yields of water radiolysis—Application to the Fricke dosimeter*, Can. J. Chem. 85,214-229 (2007).

[4] Y. Zheng, P. Cloutier, D. J. Hunting, J. R. Wagner, L. Sanche, *Glycosidic Bond Cliveage of Thymidine by Low-Energy Electrons*, JA.C.S. 126, 1002-1003 (2004).

[5] B. Boudaiffa, P. Cloutier, D. Hunting, M. A. Huels, L. Sanche, *Resonant formation of DNA Strand breaks by low-energy (3 to 20 eV) electrons*, Science, 287,1658-1660 (2000).

[6] S. Chin, et al., *The propagation of powerful femtosecond laser pulses in optical media: physics applications, and new challenges*. Can, J. Phys 83, 863-905 (2005). Review article with extensive reference.

[7] S L. Chin, S. Lagaće, *Generation of $H_2O$, $O_2$ and $H_2O_2$ from water by the use of femtosecond laser pulses and the possibility of laser sterilization*. Appl. Opt. 36, 907-911 (1996).

What is claimed is:

1. A method for generating low-energy electrons in a biological material, comprising:
   supporting the biological material;
   generating laser beam pulses; and
   focusing the laser beam pulses toward a region of interest within the biological material to generate filaments of low-energy electrons.

2. The method of claim 1, wherein the biological material is a laboratory sample.

3. The method of claim 1, wherein the biological material is contained in an aqueous solution.

4. The method of claim 1, wherein laser pulses have a wavelength of about 800 nanometers.

5. The method of claim 1, wherein laser pulses have a duration of about 100 femtosecond.

6. The method of claim 1, wherein laser pulses are repeated at a rate of about 1 kHz.

7. The method of claim 1, wherein laser pulses are generated at a power of about 300 milliwatts.

8. The method of claim 1, wherein the region of interest has a volume of about one cubic centimeter.

9. The method of claim 1, wherein the low-energy electrons have anisotropic concentrations.

10. The method of claim 1, comprising measuring a ferric ion concentration in the region of interest following generation of the low-energy electrons.

11. The method of claim 1, comprising measuring a thymine concentration in the region of interest following generation of the low-energy electrons.

12. Use of the method of claim 1 for a function selected from the group consisting of radiochemistry, sterilization, polymerization, nanoparticle coating and nanoparticle generation.

13. Use of the method of claim 1 for radiotherapy.

14. A system for generating low-energy electrons in a biological material, comprising:
   a support for the biological material;
   a pulsed laser; and
   a focusing mechanism for directing laser beam pulses toward a region of interest within the biological material to generate filaments of low-energy electrons.

15. The system of claim 14, wherein the biological material contains water.

16. The system of claim 14, wherein laser pulses have a wavelength of about 800 nanometers.

17. The system of claim 14, wherein laser pulses have a duration of about 100 femtosecond.

18. The system of claim 14, wherein laser pulses are repeated at a rate of about 1 kHz.

19. The system of claim 14, wherein laser pulses are generated at a power of about 300 milliwatts.

20. The system of claim 14, wherein the region of interest has a volume of about one cubic centimeter.

21. The system of claim 14, wherein the support is an optical path cuvette comprising a laboratory sample.

22. The system of claim 21, comprising a magnetic steering device for homogenizing a content of the cuvette.

23. The system of claim 14, wherein the low-energy electrons have anisotropic concentrations.

24. The system of claim 14, comprising a dosimeter for measuring a ferric ion concentration in the region of interest following generation of the low-energy electrons.

25. The system of claim 14, comprising a chromatograph for measuring a thymine concentration in the region of interest following generation of the low-energy electrons.

26. Use of the system of claim 14 for a function selected from the group consisting of radiochemistry, sterilization, polymerization, nanoparticle coating and nanoparticle generation.

27. Use of the system of claim 14 for radiotherapy.

* * * * *